United States Patent [19]

Suh

[11] 3,932,461
[45] Jan. 13, 1976

[54] N-[4-(3,4-METHYLENEDIOXYPHENYL)-BUT-2-YL]-β-(3,4-DIHYDROXYPHENYL)ETHYLAMINE, AND SALTS THEREOF
[75] Inventor: John T. Suh, Mequon, Wis.
[73] Assignee: Richardson-Merrell Inc., Wilton, Conn.
[22] Filed: June 28, 1974
[21] Appl. No.: 484,096

[52] U.S. Cl. .............................. 260/340.5; 424/282
[51] Int. Cl.² ....................................... C07D 317/58
[58] Field of Search ................................. 260/340.5

[56] References Cited
UNITED STATES PATENTS
3,139,441  6/1964  Biel .................................. 260/340.5
3,700,692  10/1972  Suh et al. ......................... 260/340.5

Primary Examiner—Richard L. Raymond
Attorney, Agent, or Firm—Eugene O. Retter; L. Ruth Hattan; George W. Rauchfuss, Jr.

[57] ABSTRACT

The compound N-[4-(3,4-methylenedioxyphenyl)-but-2-yl]-β-(3,4-dihydroxyphenyl)ethylamine, and salts thereof, are cardiotonic agents, central nervous system depressants and analgetic agents.

3 Claims, No Drawings

3,932,461

N-[4-(3,4-METHYLENEDIOXYPHENYL)-BUT-2-YL]-β-(3,4-DIHYDROXYPHENYL)ETHYLAMINE, AND SALTS THEREOF

BACKGROUND OF THE INVENTION

α-(3,4-Dihydroxyphenyl)-β-(N-3', 4'-methylenedioxy-phenyl)-alkylamino ethanols are disclosed in U.S. Pat. No. 3,139,441, and 1-(4'-hydroxy-3'-(hydroxymethyl)-phenyl)-1-hydroxy-2-aralkylaminoethanes are disclosed in U.S. Pat. No. 3,700,692. In addition, 3,4-dihydroxy-N-[2-(4-hydroxyphenyl) ethyl]-β-phenethylamines are disclosed in Offenlegungsschrift No. 2,317,710.

DETAILED DESCRIPTION

The compound of the present invention may be represented by the following formula:

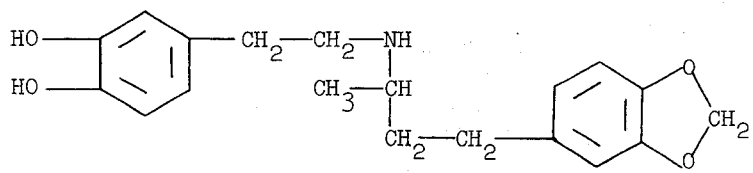

The novel compound of the present invention and its salts are useful as pharmaceutical agents because of their depressant, analgetic and cardiotonic activity. The compounds are especially interesting as cardiotonic agents. For example, in tests involving dogs, the hydrochloride salt of the compound was found, when administered intravenously at a dose of 0.3 mg/kg, to increase the contractile force of the heart selectively without significantly influencing the blood pressure or heart rate of the animal. The compound also gives indications of being orally active as a cardiotonic agent.

In animal behavioral tests the above-mentioned compound exhibited a central nervous system depressant activity. In mice receiving 30 mg/kg of the compound intraperitoneally in the form of a 5% acacia suspension, decreased alertness, reactivity, struggle response and other behavioral characteristics of central nervous system depression were observed. As a result of the behavioral studies, the compound was found to have $LD_{50}$ values in excess of 175 mg/kg. The behavioral studies were conducted in accordance with the procedure set forth by Irwin in "Animal and Clinical Pharmacologic Techniques in Drug Evaluation", J. H. Nodine and P. E. Siegler, Ed., Year Book Publishers, Inc., 1964, pp. 36–54.

The following is a description of the preferred method of preparing the compound N-(3,4-methylenedioxyphenisobutyl)-3,4-dihydroxyphenethylamine hydrochloride hydrate. Dopamine hydrochloride is dissolved in a saturated solution of sodium bicarbonate and a solution of 4-[3,4-(methylenedioxy)-phenyl]butan-2-one in ethanol is added, at which time a white precipitate forms. The thus obtained slurry is then hydrogenated for about three hours at 20 psi of hydrogen in the presence of a suitable catalyst, such as platinum oxide or 5% palladium on carbon, to form the desired compound.

Acid addition salts of the compound of the present invention may be conveniently prepared by contacting the free base form of the compound with a suitable acid such as formic acid, citric acid, maleic acid, sulfuric acid, hydrochloric acid, succinic acid, tartaric acid, benzoic acid or fumaric acid.

The preferred process of preparing the compound may be illustrated as follows:

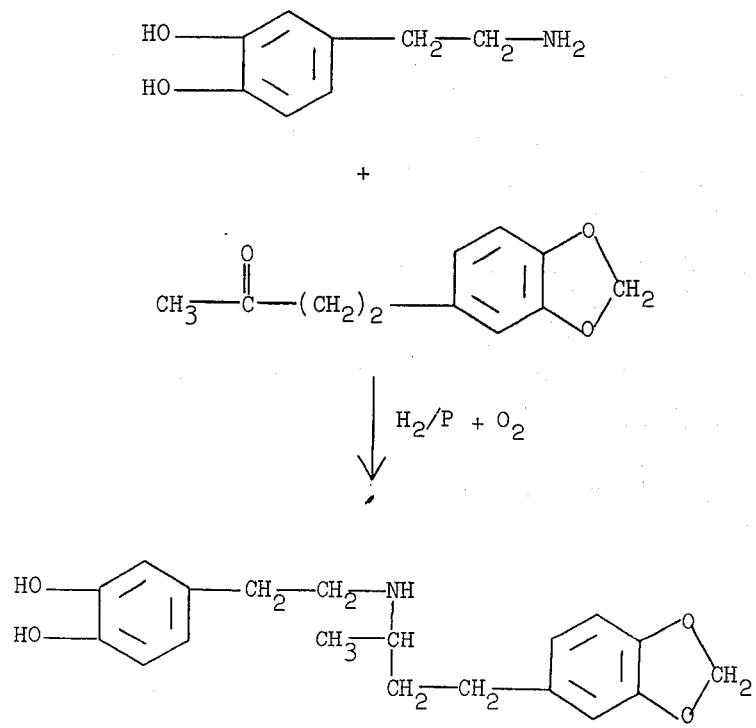

Quaternary ammonium salts may be formed by contacting the compound with a suitable alkylating agent such as dimethyl sulfate, or an alkyl halide such as methyl chloride, methyl iodide or ethyl bromide.

When intended for use as pharmaceutical agents, the compound or a salt of the compound is preferably combined with a major amount of one or more suitable pharmaceutical diluents and formed into unit dosage forms. Such dosage forms provide suitable means for oral and parenteral administration.

The pharmaceutical diluents which may be employed may be either liquid or solid, but the preferred liquid carrier is water. In the event the salt of the compound is not soluble in water, a pharmaceutically acceptable organic solvent such as propylene glycol may be employed.

Solid pharmaceutical diluents such as starch, sugar and talc can be utilized to form powders which can in turn be used as such or may be tableted or encapsulated. In addition to the forementioned material, a wide variety of conventional pharmaceutical lubricants, disintegrating agents, flavoring agents and the like may also be employed.

The unit dosage forms may contain a concentration of 0.1% to 10% or more by weight of the novel compound or one of its salts. Generally, such dosage forms will contain about 5 to 250 mg. of the active ingredients. One or more of such dosage forms may be administered daily. In actual practice, the amount of drug required to produce the desired effect will, of course, vary considerably because of patient differences.

The following example is presented to illustrate this invention:

EXAMPLE 1

N-[4-(3,4-Methylenedioxyphenyl)-but-2-yl]-β-(3,4-dihydroxyphenyl)ethylamine hydrochloride In 10 ml. of a saturated solution of sodium bicarbonate is dissolved 1.0 g. (0.00526 mole) dopamine hydrochloride. A solution of 4-[3,4-(methylenedioxy) phenyl]butan-2-one (1.10 g., 0.00526 mole) in 10 ml. ethanol is added to the above sodium bicarbonate solution. A white precipitate develops. The slurry is charged with 0.1 g. platinum oxide and hydrogenated for three hours at 20 psi. The solids are filtered and the solution concentrated. The residue is triturated with ethanol, refiltered and again concentrated. The oily residue is treated with ethereal hydrochloric acid and the so-formed solids collected and crystallized from methanol-isopropanol to give N-[4-(3,4-methylenedioxyphenyl)-but-2-yl]-β-(3,4-dihydroxyphenyl) ethylamine hydrochloride as a white solid, m.p. 204°–206°.

I claim:

1. The compound N-(3,4-methylenedioxyphenisobutyl)-3,4-dihydroxyphenethylamine, and pharmaceutically acceptable salts thereof.

2. The compound of claim 1 which is N-(3,4-methylenedioxyphenisobutyl)3,4-dihydroxyphenethylamine.

3. The compound of claim 1 which is N-(3,4-methylenedioxyphenisobutyl)3,4-dihydroxyphenethylamine hydrochloride hydrate.

* * * * *